Figure 1:
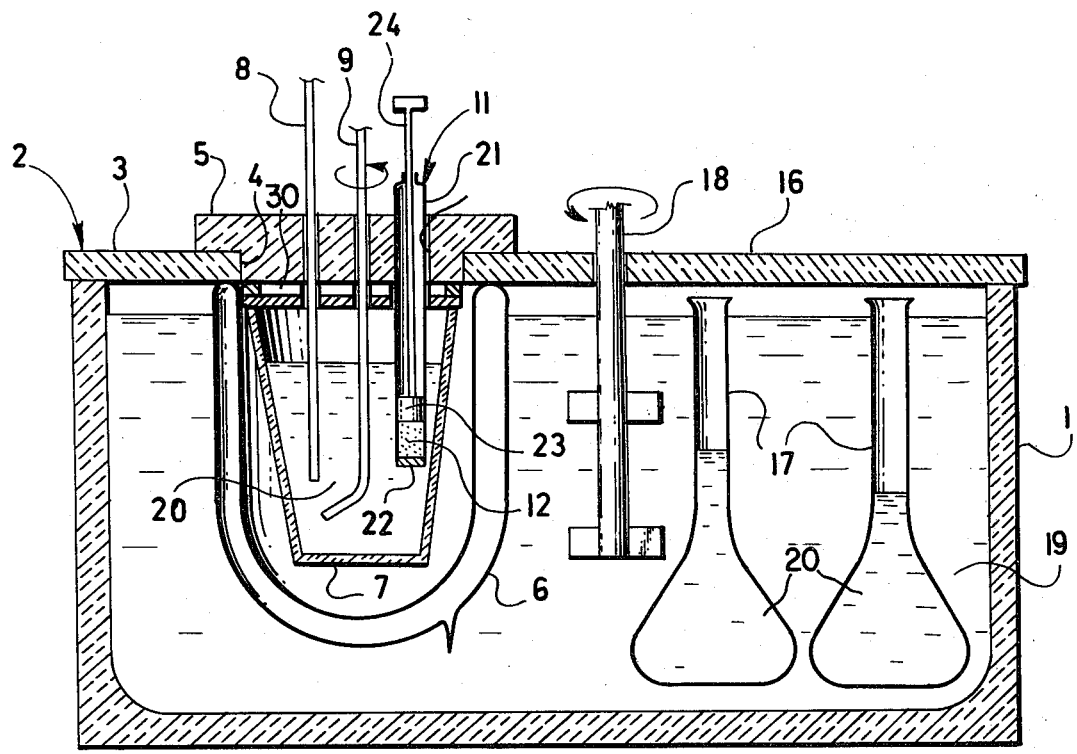

United States Patent [19]

Brandstetr et al.

[11] 4,379,775
[45] Apr. 12, 1983

[54] APPARATUS FOR THERMOCHEMICAL QUANTITATIVE ANALYSIS

[75] Inventors: Jiri Brandstetr; Josef Huleja, both of Brno; Josef Kupec, Kurim, all of Czechoslovakia

[73] Assignee: Vysoke udeni technicke, Brno, Czechoslovakia

[21] Appl. No.: 197,274

[22] Filed: Oct. 15, 1980

[51] Int. Cl.³ .................... G01K 17/00; G01N 25/20
[52] U.S. Cl. .......................................... 422/51; 374/33
[58] Field of Search ..................... 422/51; 73/190 R

[56] References Cited

U.S. PATENT DOCUMENTS

| | | | |
|---|---|---|---|
| 3,210,996 | 10/1965 | Harwood | 73/190 R |
| 3,607,089 | 9/1971 | Stoesser | 422/51 |
| 3,646,812 | 3/1972 | Ishii | 73/190 R |
| 4,130,016 | 12/1978 | Walker | 73/190 R |
| 4,152,117 | 5/1979 | Bohm | 422/51 |

*Primary Examiner*—Sidney Marantz

[57] ABSTRACT

A general-purpose apparatus for thermochemical quantitative analysis, operable upon the principle of measuring temperature variations accompanying chemical reactions between a solid and a liquid substance as well as between two solutions. An exchangeable reaction vessel made of formed polystro in Dewar vessel is received in a heat-insulated receptacle with a thermostat controlled bath, the reaction vessel being provided with a cover having an opening for a removable lid which supports a temperature sensor and a stirring rod. The removable lid has openings to receive a dose feeder for a solid specimen and/or a dose feeder for reagent solutions. Due to the equalizing of the temperature values of reagents, specimens to be analyzed, as well as the entire apparatus to a constant temperature in a thermostatically controlled bath, the apparatus according to the present invention makes it possible considerably to raise the degree of accuracy of thermochemical analysis, and to carry out a complex analysis of a single solid specimen in one solution.

4 Claims, 2 Drawing Figures

U.S. Patent

Apr. 12, 1983

4,379,775

APPARATUS FOR THERMOCHEMICAL QUANTITATIVE ANALYSIS

The present invention relates to improvements in apparatus for thermochemical quantitative analysis. Such apparatus is operable upon the principle of measuring temperature variations accompanying chemical reactions between a solid and a liquid substance as well as between two solutions.

A known apparatus of this kind consists of a pair of reaction vessels for a reaction solution, the vessels being received in a heat-insulated jacket and disposed above electromagnetic agitators. The reaction vessels are provided with covers on each of the vessels, the covers bearing a group of tubing and electrical conductors. The lifting and lowering of the covers is cared for by an electric motor via appropriate gear means. The covers are equipped with grips for securing a thermistor, three liquid dose feeders and a heater. The feeders are in the form of glass pipettes connected to a superatmospheric pressure source, more particularly a blower constituting a component of the apparatus.

A drawback of such a single-purpose apparatus is in that it allows a reagent to be supplied into the solution to be analyzed in a solution form only by a submersible dose feeder. Such a feeder, which cannot be properly controlled, has to be manually filled with a reagent outside the apparatus. Since the apparatus is not equipped with a thermostat controlled bath, both reagents and specimens have to be laboriously preheated. Accordingly, the actual analyses takes place at a non-constant temperature; this impairs the exactness of the results of the analysis. This is why it is necessary for the analysis to use relatively large volumes of the solution to be analyzed as well as reagents having high concentrations of the active substance; such practice in turn raises the consumption of chemicals. Another disadvantage of such apparatus resides in that for agitation there are employed magnetic agitation elements which, due to friction at the bottom of the reaction vessel and the electric motor itself, generate surplus heat which also may be responsible for measurement deviations. For the reasons hereinabove referred to, such an apparatus does not make it possible to carry out precise measurements of very small temperature differences, even when using sensitive temperature sensors therefor, so that the apparatus can not be used satisfactorily with very low concentrations of components in solutions. The aforedescribed apparatus is also incapable to process or supply solid specimens, suspensions, or viscous liquids to the solution to be analyzed.

To eliminate the drawbacks of the prior art as herein above referred to, it is an object of the invention to provide an improved apparatus for thermochemical quantitative analysis. The apparatus according to the invention comprises a reaction vessel in a Dewar vessel received in a heat-insulated receptacle with a thermostat controlled bath, said receptacle being provided with a cover having an opening for a removable lid with a temperature sensor, a stirring rod, and beds for a dose feeders of solid specimens and/or at least one liquid dose feeder.

The solid specimen dose feeder may be embodied as a cylindrical container closed at one end by a plug and provided in its interior with a piston connected to a piston rod.

The liquid dose feeder may be embodied as a flask with an ascending neck in which there is inserted for adjustable shifting a dosing tube the opposite end of which is received in a reagent stock bottle; said flask is provided with an overflow pipe one end of which is outside the flask and the opposite end is inside the flask at the bottom thereof.

An advantage of the apparatus according to the invention is that the apparatus allows the exactness of the analysis results to be improved due to the thermostat controlled bath in which both reagents in stock bottles and the specimens in volumetric flasks are placed, so that the solutions as well as the parts of the apparatus are heated or cooled to the same constant temperature. By locating the stirred elements above the removable lid with insulating air layer, the influence of the heat generated is reduced to a minimum. The method of direct injection thermochemical analysis for which the apparatus has been designed, is especially suitable for use in the cases wherein other methods are considerably time-consuming as, for example, when determining sulphates, silicon, fluorides or the like. Owing to the simplicity and to relatively low initial cost of the apparatus, such method and apparatus can be easily availed of in small producing plants for routine analyses.

By making the measurement more precise, it is possible to reduce the volume of the solution to be analyzed and thus to use a small-capacity reaction vessel. Apart from this, lower concentrations of active substance in the solution to be analyzed as well as of reagents can be employed.

The structure of the removable lid allows the use of various types of submersible feeders for dosing both liquid and/or solid substances. It is also possible simultaneously to employ various types of dose feeders in one and the same reaction vessel if a complex analysis of a single specimen is to be carried out. The liquid dose feeder can be filled semi-automatically with a predetermined volume of a solution without the necessity of taking it out of the removable lid. The apparatus of the invention enables the use of lightweight materials for the reaction vessels to be made of, such as, for instance, foamed polystyrene, whereby the reproducibility of measurement is considerably improved. The reaction vessels need not be heat-insulated, in the thermostat controlled bath there can be also installed other additional appliances for thermochemical analysis such as for throughflow, titration or the like analysis.

Figure 2:
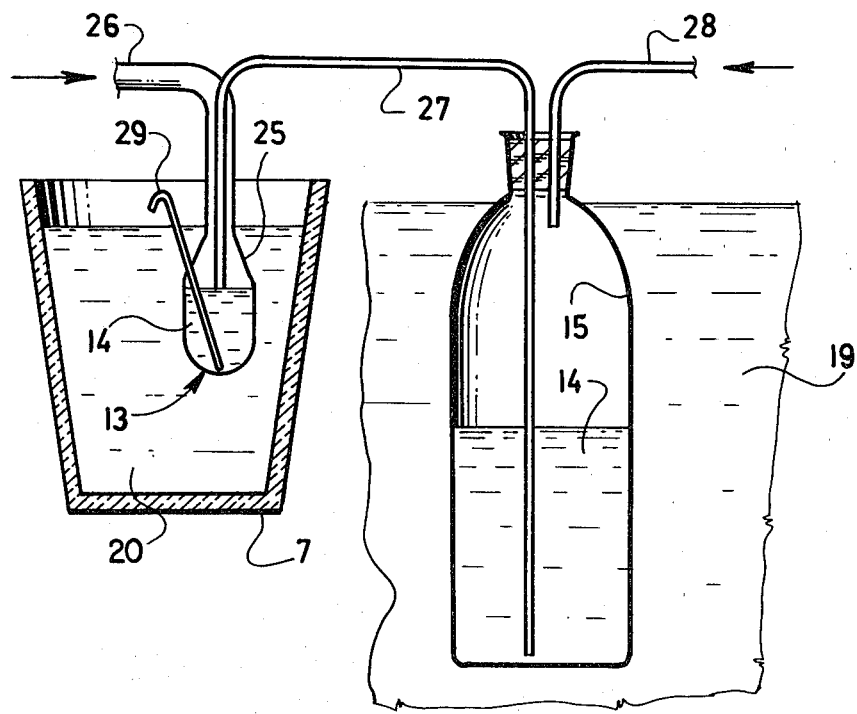

A preferred embodiment of the apparatus according to the invention is hereinafter described with reference to the accompanying drawings, in which:

FIG. 1 is a vertical sectional view of a first embodiment of the apparatus, such embodiment having a dose feeder which is shown feeding a solid specimen to the reaction vessel, and FIG. 2 is a fragmentary vertical sectional view of a second embodiment of the apparatus, the reaction vessel having a liquid reagent dose feeder with a stock bottle.

Turning first to FIG. 1, the apparatus comprises a heat-insulated receptacle 1 which may have, for example, a double wall, although the wall thereof is here shown as a single wall. The receptacle 1 is provided with a cover generally designated 2 a part 3 of which is stationary and has an opening 4 thereinclosed by a removable lid 5. Under said lid 5 the receptacle 1 accommodates a Dewar (double-walled vacuum) vessel 6 receiving an upwardly open reaction vessel 7 made, for instance, of foamed polystyrene. In said removable lid 5 with an insulating air layer 30 there are inserted a temperature sensor 8, a rotatable stirring rod 9 connected to a drive unit (not shown), and an opening 10 designed to receive a dose feeder 11 which is shown dosing a solid specimen 12. The receptacle 1 contains a thermostat controlled liquid bath 19. A part 16 of the generally stationary cover portion 3 is attached to receptacle 1 by hinges (not shown). The inner space of the receptacle 1 below said hinged cover portion 16 is designed for equalizing the temperature of a set of volumetric flasks 17 containing reacting liquid 20, which can be constituted by a reagent solution or a liquid specimen.

The receptacle 1 is further provided with a rotatable agitator 18 for stirring the thermostat controlled bath 19. The rotatable stirring rod 9 is designed for stirring only the contents 20 of the reaction vessel 7.

The dose feeder 11, which is shown dosing the solid specimen 12, is made as an elongated cylindrical container 21 closed at its lower extremity by a removable plug 22 between which and a piston 23 inserted in the container 21 a solid comminuted specimen 12 is located. The piston 23 is provided with a piston rod 24 extending out from the upper end of the cylindrical container 21. It is to be understood that the dose feeder 11 may also be employed to dose or feed a measured quantity of liquid specimen, suspension, emulsion or reagent into the reaction vessel.

The above-described apparatus operates as follows:

A reagent 20 is poured into the reaction vessel 7 and a dose feeder 11 with a specimen 12, which may be either solid or liquid, is introduced into the opening 10 in the removable lid 5. The reaction vessel 7 is put in the Dewar vessel 6 submerged in the thermostat controlled bath 19. Alternatively, the reaction vessel 7 can be put immediately into the thermostat controlled bath which is heated by means of a heating element (not shown) controlled by a thermostat (not shown) to a temperature predetermined in dependence upon the type of analysis to be performed. After the removable lid 5 has been inserted into the opening 4 in the stationary cover 3 of the receptacle 1, an electric motor (not shown) which drives the stirring rod 9 is set in operation, which rod, by agitating the contents of the reaction vessel 7, equalizes the temperature values of the reaction vessel 7, the reagent 20, and the dose feeder 11 with, in this case, the solid specimen 12. After the temperatures have been equalized, the piston rod 24 together with the piston 23 is manually pushed down, whereby the solid specimen 12 together with the plug 22 is pressed out of the cylindrical container 21 of the dose feeder 11 into the reagent 20. Due to the action of the reagent 20 on the solid specimen 12, the particular chemical reaction takes place, and the heat generated thereby will then heat the contents of the reaction vessel 7, the resultant temperature variation recorded by the temperature sensor 8 being directly proportional to the amount of chemical substance analyzed.

Turning now to FIG. 2, there is there shown a dose feeder 13 for dosing a liquid reagent 14, the latter being interconnected by a tube 27 with a stock bottle 15 with a reagent 14, the stock bottle and its contents being received in the thermostat controlled bath 19.

It is to be understood that the thermostat controlled bath 19 of FIG. 2 is contained in a receptacle similar to receptacle 1 of FIG. 1, and that the parts shown in FIG. 2, that is, the reaction vessel 7 and its contents, the stock bottle 15 and its contents are all disposed in a heat-insulated receptacle similar to receptacle 1 of FIG. 1. It is also to be understood that such heat-insulated receptacle employed in FIG. 2 has a cover and a lid similar to those in FIG. 1, and that the lid supports at least one other dose feeder the temperature sensor and a stirrer for the reaction liquid, such elements being similar to elements 8 and 9, respectively, in FIG. 1.

The apparatus according to FIG. 2 operates in such manner that a liquid specimen 20 is poured into the reaction vessel 7 while the liquid dose feeder 13 for the reagent 14 is introduced into the opening 10 of the removable lid 5. The liquid dose feeder 13 is then filled up by supplying pressurized air through a tube 28 into the stock bottle 15 from which, due to a superatmospheric pressure, the reagent 14 will overflow via dosing hose 27 into the flask 25 of the liquid dose feeder 13. The desired dose amount of reagent 14 can be controlled by the depth of immersion of the dosing hose 27 into the flask 25. If the pressure air supply is cut off and an overpressure is released by a valve (not shown), a reagent excess above the end of the dosing hose 27, owing to uneven levels of the reagent 14 in the liquid dose feeder 13 and in the stock bottle 15, will flow back to such stock bottle 15. After the temperatures of the reaction vessel 7 with the liquid specimen 20 and of the liquid dose feeder 13 with reagent 14 have been equalized, a metered dose of reagent 14, by the introduction into the flask 25 of pressurized air by way of ascending pipe 26, is forced through the overflow pipe 29 into the liquid specimen 20 in the reaction vessel 7. An exothermic or endothermic reaction will then take place in the reaction vessel. In a manner similar to that in the apparatus of FIG. 1, a measured temperature difference is directly proportional to the amount of chemical substance analyzed.

The apparatus according to the present invention can be availed of for carrying out thermochemical quantitative analysis as well as some specific physico-chemical measurements such as, for example, for measuring the dilution, dissolution, adsorption, absorption heat values and the like of various reactions.

Although the invention has been illustrated and described with the preference to a plurality of preferred embodiments thereof, it is to be expressly understood that it is in no way limited to the disclosure of such embodiments, but is capable of numerous modifications within the scope of the appended claims.

We claim:

1. An apparatus for thermochemical quantitative analysis, comprising a heat-insulated receptacle with a thermostatically controlled liquid bath, a removable part and a hinged part, the receptacle containing a Dewar vessel in which there is an exchangable reaction vessel, the receptacle further containing at least one stock bottle and at least one volumetric flask which are disposed below the hinged part of the lid and contain a solution to be analyzed and a reagent solution, respectively, the removable part of the lid which has the air-filled insulating space being retained by gravity above said reaction vessel and being provided with apertures for at least one liquid reagent dose feeder and a dose feeder for a solid sample.

2. An apparatus as claimed in claim 1, wherein the exchangeable reaction vessel is made of foamed polystyrene.

3. An apparatus as claimed in claim 1, wherein the solid specimen dose feeder is a cylindrical container closed at its lower end by a plug for retaining a solid specimen, the container receiving a piston rod with a piston for discharging the solid specimen together with the plug out of the container into said reaction vessel.

4. An apparatus as claimed in claim 1, wherein the liquid specimen dose feeder is a flask made of thermoplastic material, said flask having a neck for passing a vertically displaceable U-shaped pipe extending by one of its ends to an arbitrary depth down into said flask, while the other end of the pipe is disposed at the bottom of the stock bottle in a water bath, said stock bottle containing a reagent solution, said bottle being provided with a pipe adapted to be connected to a superatmospheric pressure source.

* * * * *